United States Patent [19]

Clay

[11] Patent Number: 4,506,404

[45] Date of Patent: Mar. 26, 1985

[54] DISPOSABLE SPONGE

[76] Inventor: Ambrose W. J. Clay, P.O. Box 22642, Nashville, Tenn. 37202

[21] Appl. No.: 463,039

[22] Filed: May 11, 1983

[51] Int. Cl.[3] .............................................. A47L 13/16
[52] U.S. Cl. .................. 15/244 C; 15/218.1
[58] Field of Search ............ 15/244 R, 244 B, 244 C, 15/210 A, 210 B, 218.1

[56] References Cited

U.S. PATENT DOCUMENTS

| | | | |
|---|---|---|---|
| 2,483,593 | 10/1949 | Novick | 15/244 R X |
| 2,846,708 | 8/1958 | Vosbikian et al. | 15/244 R |
| 3,041,651 | 7/1962 | Jardine | 15/244 R |
| 3,161,903 | 12/1964 | Worthington | 15/244 R X |
| 3,570,036 | 3/1971 | Gilchrist et al. | 15/244 R X |
| 4,077,083 | 3/1978 | Siemund et al. | 15/244 R |

FOREIGN PATENT DOCUMENTS 1434159  2/1966  France ............................. 15/244 R

*Primary Examiner*—Chris K. Moore
*Attorney, Agent, or Firm*—Harrington A. Lackey

[57] ABSTRACT

A disposable sponge device used principally for cleaning surgical instruments and including a flexible base sponge member having opposed side and end edges and a pair of upright flexible sponge members attached to and projecting from the back surface of the base sponge member, substantially parallel to each other, and extending end-to-end of the base sponge member to function as a handle for the sponge device. The sponge device is further characterized by including, along at least one edge portion, an elongated slit opening through the edge portion for receiving the blade of a surgical instrument for cleaning.

3 Claims, 4 Drawing Figures

DISPOSABLE SPONGE

BACKGROUND OF THE INVENTION

This invention relates to a sponge device, and more particularly a cleaning sponge device primarily for use in the surgical field.

SUMMARY OF THE INVENTION

It is an object of this invention to provide a disposable sponge device for use in a sterile operating field, and particularly for use in cleaning dirty, bloody instruments utilized in the course of performing surgical procedures in an operating room.

The sponge device is made of any type of elastic porous mass of acceptable fibers, or porous rubberized materials, and is capable of absorbing water and being wrung dry.

The sponge device, made in accordance with this invention, includes a flexible base sponge member and a pair of upright elongated flexible sponge members integrally attached to, and forming a part of, the base sponge member. An elongated miniature slit is formed in either side edge portion of the base sponge member for receiving and cleaning the blade portion of a surgical instrument, such as a scalpel blade.

The sponge device is designed for cleaning surgical instruments, such as a scalpel, either by running the blade of the instrument along and through the slit formed in the edge portion of the base member, or by grasping the upright sponge members in one hand while cleaning with the base sponge member.

DESCRIPTION OF THE PREFERRED EMBODIMENT

Figure 1:
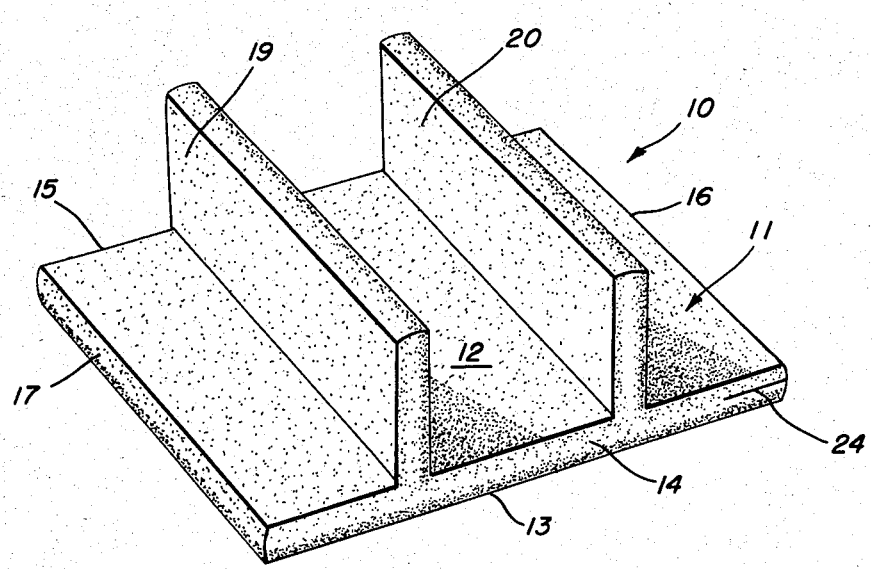
FIG. 1 is a left, front, top perspective view of the sponge device made in accordance with this invention.

Referring now to the drawings in more detail, the disposable sponge device 10, made in accordance with this invention, includes a base sponge member 11, of predetermined thickness, and illustrated in FIG. 1 as having a substantially rectangular or square configuration, a top or back surface 12, a bottom or face surface 13, a front end edge portion 14, a rear end edge portion 15, a right side edge portion 16, and a left side edge portion 17.

Projecting upward away from the top surface 12, and preferably forming an integral part of the base sponge member 11, are a pair of elongated upright sponge members 19 and 20. Each of the upright sponge members 19 and 20 is shown as substantially rectangular and extending from end-to-end the full length of the base member 11.

Figure 4:
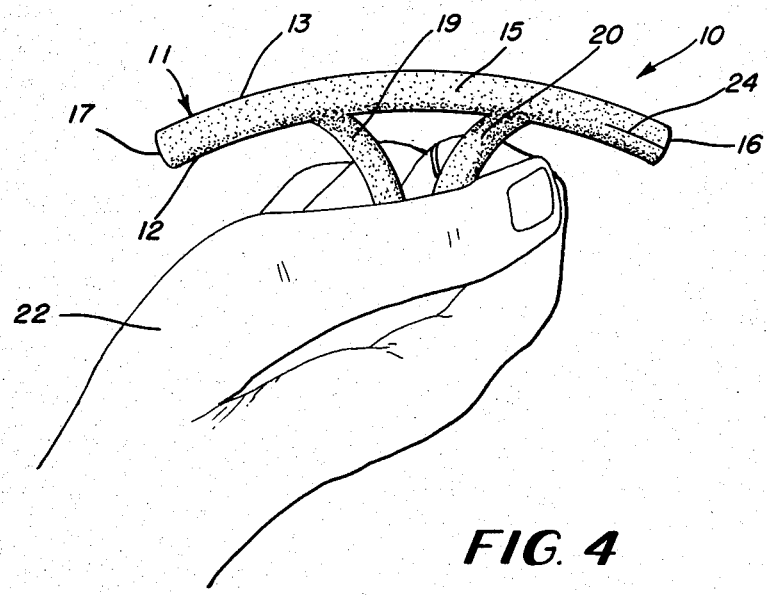
FIG. 4 is a rear elevational view of the device, upside down, in an operative position gripped by the hand of the user.

The upright members 19 and 20 are spaced apart, parallel to each other, and spaced between the opposite side edge portions 16 and 17. As illustrated in FIG. 4, the upright members 19 and 20 should be spaced close enough that they may be grasped simultaneously and squeezed against each other by the hand 22 of the user. When the upright members 19 and 20 are grasped and squeezed together by the hand 22, as illustrated in FIG. 4, the base member 11 is contracted into an arcuate shape, as shown in FIG. 4, to present the bottom surface 13 in an arcuate plane.

Formed in at least one edge portion of the base member 11 is an elongated slit 24. In the drawings, the slit 24 is formed longitudinally in and along the right side edge portion 16, and between the top surface 12 and bottom surface 13 of the base member 11. As illustrated in the drawings, the slit 24 extends end-to-end of the base member 11 and opens through both front and rear edge portions 14 and 15, as well as opening along the right side edge portion 16.

The function of the slit 24 is to receive therein the blade portion of a surgical instrument, such as the blade of a scalpel. By placing the dull side of the blade, not shown, into the slit 24 and then pulling the handle of the scalpel longitudinally of the slit 24, while simultaneously pressing down on top of the base sponge member 11, both sides of the blade are cleaned.

The sponge device 10 may also be used to clean serrated instruments by use of the flexible sponge members 19 and 20 attached to the base sponge member 11.

The material from which the sponge device 10 is made, that is the base sponge member 11 and also the upright sponge members 19 and 20, may be an elastic porous mass of acceptable fibers, or porous rubberized materials, with the ability to absorb water.

The slit 24 may extend partially or entirely throughout the lateral aspect of base sponge member 11.

The sponge device 10 may be used for cleaning purposes in the sterile field, or may be used outside of the sterile field, upon completion of the surgical operation, for cleaning unsterile instruments.

Figures 2, 3:
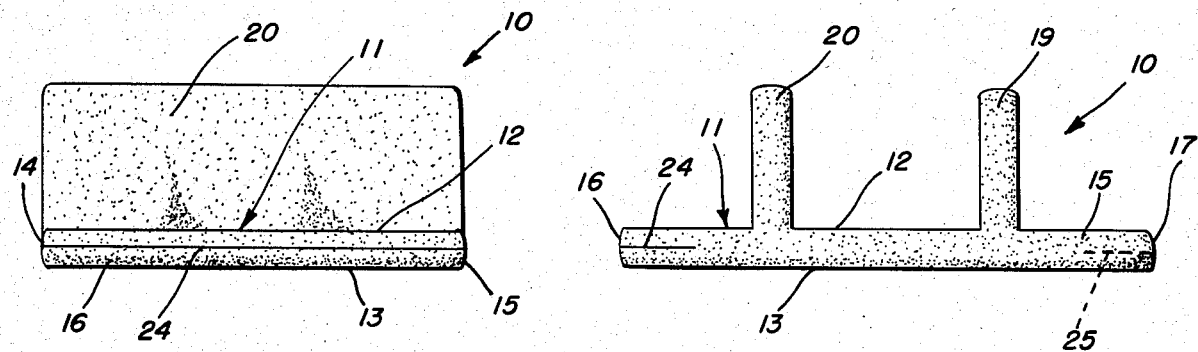
FIG. 2 is a right end elevation of the sponge device disclosed in FIG. 1.
FIG. 3 is a rear elevational view of the device disclosed in FIG. 1.

Furthermore, the opposite side edge portion 17 may include a slit 25, illustrated in phantom in FIG. 3, in addition to, or instead of the slit 24. The slit 25 will have the same construction as the slit 24.

The material of the sponge device 10 is also made of material which is so economical that it may be disposed of.

I claim:

1. A disposable sponge device comprising:
    (a) a base sponge member of flexible material and predetermined thickness, having a face surface, a back surface, opposed end edge portions, and opposed side edge portions,
    (b) first and second elongated upright sponge members of flexible material attached to and projecting from said back surface, said upright sponge members extending end-to-end of said base sponge member,
    (c) said upright sponge members being spaced from each other and between said opposed side edge portions sufficiently that both said upright sponge members can be grasped and pulled toward and against each other by a single hand of the user of the sponge device, and
    (d) an elongated slit formed in one edge portion of said base sponge member between said top and bottom surfaces and opening through at least said one edge portion, for receiving the edge of a blade for cleaning the blade.

2. The invention according to claim 1 in which said slit is formed in, and extends along, one of said side edge portions.

3. The invention according to claim 1 in which said first and second upright sponge members are elongated and extend substantially parallel to each other along said back surface.

* * * * *